US009198676B2

(12) United States Patent
Pilgeram et al.

(10) Patent No.: US 9,198,676 B2
(45) Date of Patent: Dec. 1, 2015

(54) PCL GUIDES FOR DRILLING TIBIAL AND FEMORAL TUNNELS

(75) Inventors: Kyle Craig Pilgeram, San Jose, CA (US); Ran Oren, Kibbutz Gaaton (IL); Eran Zakai, Misgav (IL); Elad Rash, Beit Lehem Haglilit (IL)

(73) Assignee: Howmedica Osteonics Corp., Mahwah, NJ (US)

( * ) Notice: Subject to any disclaimer, the term of this patent is extended or adjusted under 35 U.S.C. 154(b) by 316 days.

(21) Appl. No.: 13/190,846

(22) Filed: Jul. 26, 2011

(65) Prior Publication Data

US 2013/0030442 A1    Jan. 31, 2013

(51) Int. Cl.
*A61B 17/17*    (2006.01)

(52) U.S. Cl.
CPC ......... *A61B 17/1714* (2013.01); *A61B 17/1764* (2013.01)

(58) Field of Classification Search
CPC ............ A61B 17/17; A61B 17/1703–17/1735; A61B 17/1739; A61B 17/1764
USPC ....................... 606/86 R, 87–89, 96–98, 102; 623/13.11–13.19
See application file for complete search history.

(56) References Cited

U.S. PATENT DOCUMENTS

| | | |
|---|---|---|
| 2,697,433 A | 12/1954 | Zehnder |
| 4,444,180 A | 4/1984 | Schneider et al. |
| 4,535,768 A | 8/1985 | Hourahane et al. |
| 4,672,957 A | 6/1987 | Hourahane |
| 4,708,139 A | 11/1987 | Dunbar, IV |
| 4,722,331 A | 2/1988 | Fox |
| 4,739,751 A | 4/1988 | Sapega et al. |
| 4,781,182 A | 11/1988 | Purnell et al. |
| 4,784,126 A | 11/1988 | Hourahane |
| 4,787,377 A | 11/1988 | Laboureau |
| 4,862,882 A | 9/1989 | Venturi et al. |
| 4,883,048 A | 11/1989 | Purnell et al. |
| 4,920,958 A | 5/1990 | Walt et al. |
| 4,922,897 A | 5/1990 | Sapega et al. |
| 5,112,335 A | 5/1992 | Laboureau et al. |
| 5,112,337 A | 5/1992 | Paulos et al. |
| 5,139,520 A | 8/1992 | Rosenberg |
| 5,154,720 A | 10/1992 | Trott et al. |
| 5,163,940 A | 11/1992 | Bourque |
| 5,211,647 A | 5/1993 | Schmieding |
| 5,217,463 A | 6/1993 | Mikhail |
| 5,267,786 A | 12/1993 | Aisley |

(Continued)

FOREIGN PATENT DOCUMENTS

EP            350780 A1    1/1990

*Primary Examiner* — Anu Ramana
*Assistant Examiner* — Jessica Weiss
(74) *Attorney, Agent, or Firm* — Lerner, David, Littenberg, Krumholz & Mentlik, LLP

(57) ABSTRACT

Disclosed are femoral and tibial drill guides for use in posterior cruciate ligament replacement surgery. Each of the drill guides includes an arc shaped member and an elongate guide member, a stopper member, and an alignment arm member coupled thereto. Prior to preparing a tibial tunnel with a tibial drill guide and a femoral tunnel with a femoral drill guide, a rasp and/or cutter can be used to remove any remnants of the posterior cruciate ligament left prior to replacement thereof. The tibial drill guide includes a concave blocking surface and a viewing aperture on the alignment arm member to block the advancement and view the location of a guide pin exiting from a posterior portion of a tibia, respectively.

19 Claims, 10 Drawing Sheets

(56) References Cited

U.S. PATENT DOCUMENTS

| | | | |
|---|---|---|---|
| 5,269,786 A | 12/1993 | Morgan | |
| 5,300,077 A | 4/1994 | Howell | |
| 5,308,349 A | 5/1994 | Mikhail | |
| 5,308,350 A | 5/1994 | Mikhail | |
| 5,312,412 A | 5/1994 | Whipple | |
| 5,320,626 A | 6/1994 | Schmieding | |
| 5,330,468 A | 7/1994 | Burkhart | |
| 5,334,194 A | 8/1994 | Mikhail | |
| 5,334,205 A | 8/1994 | Cain | |
| 5,350,383 A * | 9/1994 | Schmieding et al. | 606/96 |
| 5,374,269 A | 12/1994 | Rosenberg | |
| 5,380,331 A | 1/1995 | Mikhail | |
| 5,397,330 A | 3/1995 | Mikhail | |
| 5,409,494 A | 4/1995 | Morgan | |
| 5,425,733 A | 6/1995 | Schmieding | |
| 5,445,642 A | 8/1995 | McNulty et al. | |
| 5,458,602 A * | 10/1995 | Goble et al. | 606/96 |
| 5,458,604 A | 10/1995 | Schmieding | |
| 5,562,664 A | 10/1996 | Durlacher et al. | |
| 5,573,538 A | 11/1996 | Laboureau | |
| 5,584,839 A | 12/1996 | Gieringer | |
| 5,601,550 A | 2/1997 | Esser | |
| 5,613,971 A | 3/1997 | Lower et al. | |
| 5,643,273 A | 7/1997 | Clark | |
| 5,681,320 A | 10/1997 | McGuire | |
| 5,683,400 A | 11/1997 | McGuire | |
| 5,688,284 A | 11/1997 | Chervitz et al. | |
| 5,968,050 A | 10/1999 | Torrie | |
| 6,019,767 A | 2/2000 | Howell | |
| 6,120,511 A | 9/2000 | Chan | |
| 6,187,011 B1 | 2/2001 | Torrie | |
| 6,210,415 B1 | 4/2001 | Bester | |
| 6,254,604 B1 | 7/2001 | Howell | |
| 6,254,605 B1 | 7/2001 | Howell | |
| 6,254,606 B1 | 7/2001 | Carney et al. | |
| 6,375,658 B1 | 4/2002 | Hangody et al. | |
| 6,669,698 B1 | 12/2003 | Tromanhauser et al. | |
| 6,918,916 B2 | 7/2005 | Gobel et al. | |
| 7,160,305 B2 | 1/2007 | Schmieding | |
| 7,192,432 B2 | 3/2007 | Wetzler et al. | |
| 7,201,756 B2 | 4/2007 | Ross et al. | |
| 7,238,189 B2 | 7/2007 | Schmieding et al. | |
| 7,575,578 B2 | 8/2009 | Wetzler et al. | |
| 7,578,824 B2 | 8/2009 | Justin et al. | |
| 7,842,042 B2 | 11/2010 | Reay-Young et al. | |
| 2003/0216742 A1 | 11/2003 | Wetzler et al. | |
| 2004/0176771 A1 | 9/2004 | Schmieding | |
| 2004/0193172 A1 | 9/2004 | Ross et al. | |
| 2005/0177171 A1 | 8/2005 | Wetzler et al. | |
| 2006/0009774 A1 | 1/2006 | Goble et al. | |
| 2006/0111726 A1 | 5/2006 | Felt et al. | |
| 2006/0195112 A1 | 8/2006 | Ek | |
| 2006/0271059 A1 | 11/2006 | Reay-Young et al. | |
| 2007/0233128 A1 | 10/2007 | Schmieding et al. | |
| 2007/0233151 A1 | 10/2007 | Chudik | |
| 2007/0250067 A1 | 10/2007 | Schmieding et al. | |
| 2009/0143784 A1 | 6/2009 | Petersen et al. | |
| 2009/0171360 A1 * | 7/2009 | Whelan | 606/88 |
| 2009/0216236 A1 | 8/2009 | Re | |
| 2010/0010497 A1 | 1/2010 | Goble et al. | |
| 2010/0049196 A1 | 2/2010 | Re | |
| 2010/0049197 A1 | 2/2010 | Re | |
| 2010/0049198 A1 | 2/2010 | Re | |
| 2010/0049199 A1 | 2/2010 | Re | |
| 2010/0121337 A1 | 5/2010 | Pandya | |
| 2010/0121338 A1 | 5/2010 | Pandya | |
| 2010/0191247 A1 | 7/2010 | Schneider | |
| 2010/0256642 A1 | 10/2010 | Stone | |
| 2011/0034933 A1 | 2/2011 | Paulos | |
| 2011/0251621 A1 * | 10/2011 | Sluss et al. | 606/96 |
| 2012/0109136 A1 | 5/2012 | Bourque et al. | |
| 2012/0197259 A1 | 8/2012 | Smith | |

\* cited by examiner

PCL GUIDES FOR DRILLING TIBIAL AND FEMORAL TUNNELS

FIELD OF THE INVENTION

The present invention relates to orthopedic instruments for use during arthroscopic surgery, and more particularly, to femoral and tibial drill guides for accurately and safely drilling femoral and tibial tunnels respectively in PCL replacement surgery.

BACKGROUND OF THE INVENTION

The posterior cruciate ligament (PCL) is located in the back part of the knee joint and connects the tibia and the femur. The PCL can be torn when the knee is abnormally twisted. PCL replacement surgery may be necessary if conventional treatment, such as physical therapy, will not bring back basic function of the PCL prior to injury thereof.

During PCL replacement surgery, an orthopedic surgeon generally replaces the damaged ligament with a graft. After making one or more incisions through the skin of a patient, the surgeon inspects the knee joint and generally removes any remnants of the PCL using an arthroscopic shaver. Tibial and femoral tunnels are then drilled in the tibia and femur respectively in order to provide access locations to anchor the graft. In order to position and tension the graft accurately, the tunnels are drilled using drill guides.

A tibial tunnel is generally drilled diagonally from an anterior portion and exiting a posterior portion of the tibia at a predetermined distance below the tibia plateau. Adjacent the posterior portion of the tibia are delicate tissues such as the popliteal artery and femoral nerve, for example. As a guide pin or drill exits the posterior portion of the tibia after formation of the tibial tunnel, care should be taken by the surgeon so as to not contact and potentially damage these tissues.

The femoral tunnel is generally drilled diagonally from a posterior portion of the femur and exiting an anterior portion of the femur between the femoral condyles. The graft is then generally attached to long sutures and pulled into position through the tibial and femoral tunnels. The graft replacement is generally held into place by bioabsorbable or metallic screws.

While it is important for the surgeon to be able to view the exit location of a guide pin or drill from the posterior portion of a patient's tibia, there exists a need to ensure that delicate tissues, such as the popliteal artery and the femoral nerve, for example, are not damaged as the guide pin or drill exits the tibia.

BRIEF SUMMARY OF THE INVENTION

A first aspect of the present invention is a drill guide for arthroscopic surgery comprising an arc shaped member, an elongate guide member coupled to the arc shaped member, the elongate guide member having a bore hole therethrough for receiving a guide pin, the bore hole defining a longitudinal axis, and an alignment arm member having a first end portion and a second end portion, the first end portion coupled to the arc shaped member and the second end portion having a concave blocking surface for blocking the guide pin from moving any further in the bore hole in a distal direction, the concave blocking surface having a central axis coaxially aligned with the longitudinal axis of the bore hole of the elongate guide member.

In accordance with one embodiment of this first aspect of the present invention, the alignment arm includes a viewing aperture adjacent the concave blocking surface, the viewing aperture having an axis that intersects the central axis of the concave blocking surface at an angle.

In accordance with another embodiment of this first aspect, the drill guide further includes a stopper member pivotably coupled to the arc shaped member. The stopper member preferably includes an open slot at a first end thereof, the open slot adapted to house the guide pin therethrough.

A second aspect of the present invention is a method of drilling a tibial tunnel in a tibia for arthroscopic ligament reconstruction using a drill guide, the drill guide including an arc shaped member, an elongate guide member coupled to the arc shaped member, the elongate guide member having a bore hole therethrough, the bore hole defining a longitudinal axis and being adapted to receive a guide pin for preparing the tibial tunnel position, and an alignment arm member having a having a first end portion and a second end portion, the first end portion coupled to the arc shaped member and the second end portion having a concave blocking surface, the concave blocking surface having a central axis coaxially aligned with the longitudinal axis of the bore hole of the elongate guide member.

The method includes the steps of engaging a posterior portion of the tibia with a marking tip terminating at the first end of the alignment arm member, engaging an anterior portion of the tibia with an open tip terminating at a distal portion of the elongate guide member, inserting a guide pin into and through the bore hole of the elongate guide member, and advancing the guide pin through the tibia along the longitudinal axis defined by the bore hole until a distal tip of the guide pin contacts the concave blocking surface of the alignment arm member.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION

As used herein, when referring to the drill guides of the present invention, the term "proximal" means closer to the surgeon or in a direction toward the surgeon and the term "distal" means more distant from the surgeon or in a direction away from the surgeon. The term "anterior" means towards the front part of the body or the face and the term "posterior" means towards the back of the body. The term "medial" means toward the midline of the body and the term "lateral" means away from the midline of the body.

Figure 1:
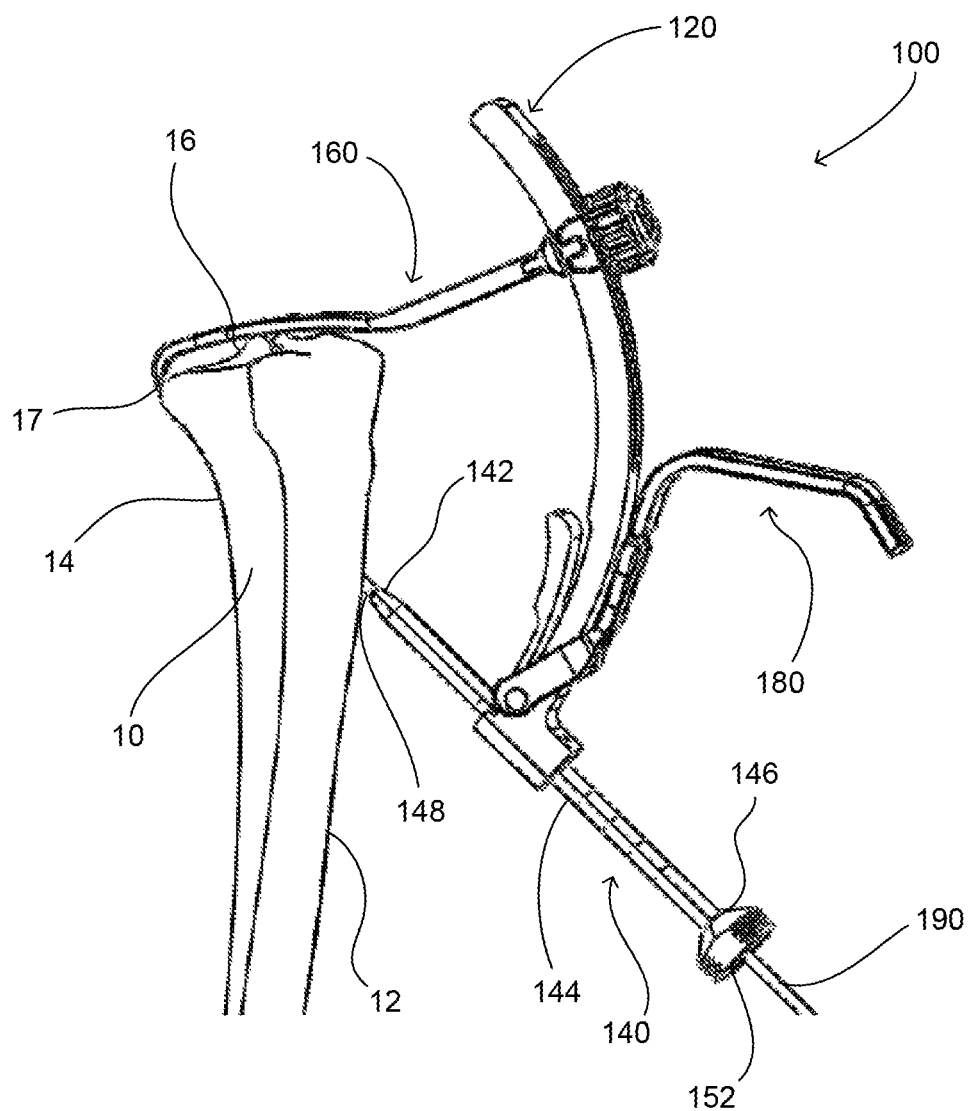
FIG. 1 is a perspective view of a tibial tunnel guide having an arc shaped member, an elongate guide member, a tibial alignment arm member and a stopper member.
Figure 2:
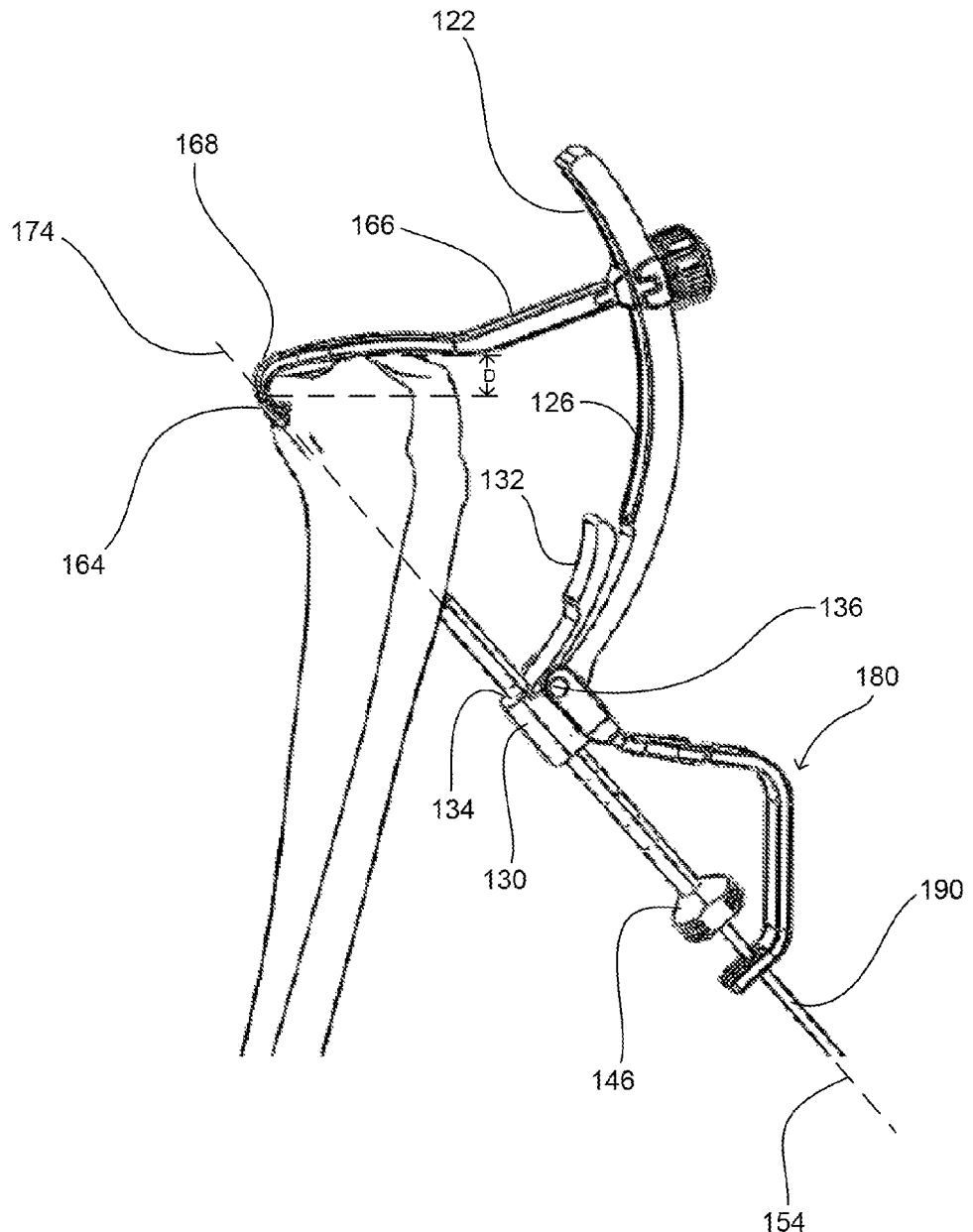
FIG. 2 is an alternate perspective view of the tibial tunnel guide of FIG. 1 with the stopper member in a deployed position.
Figure 3:
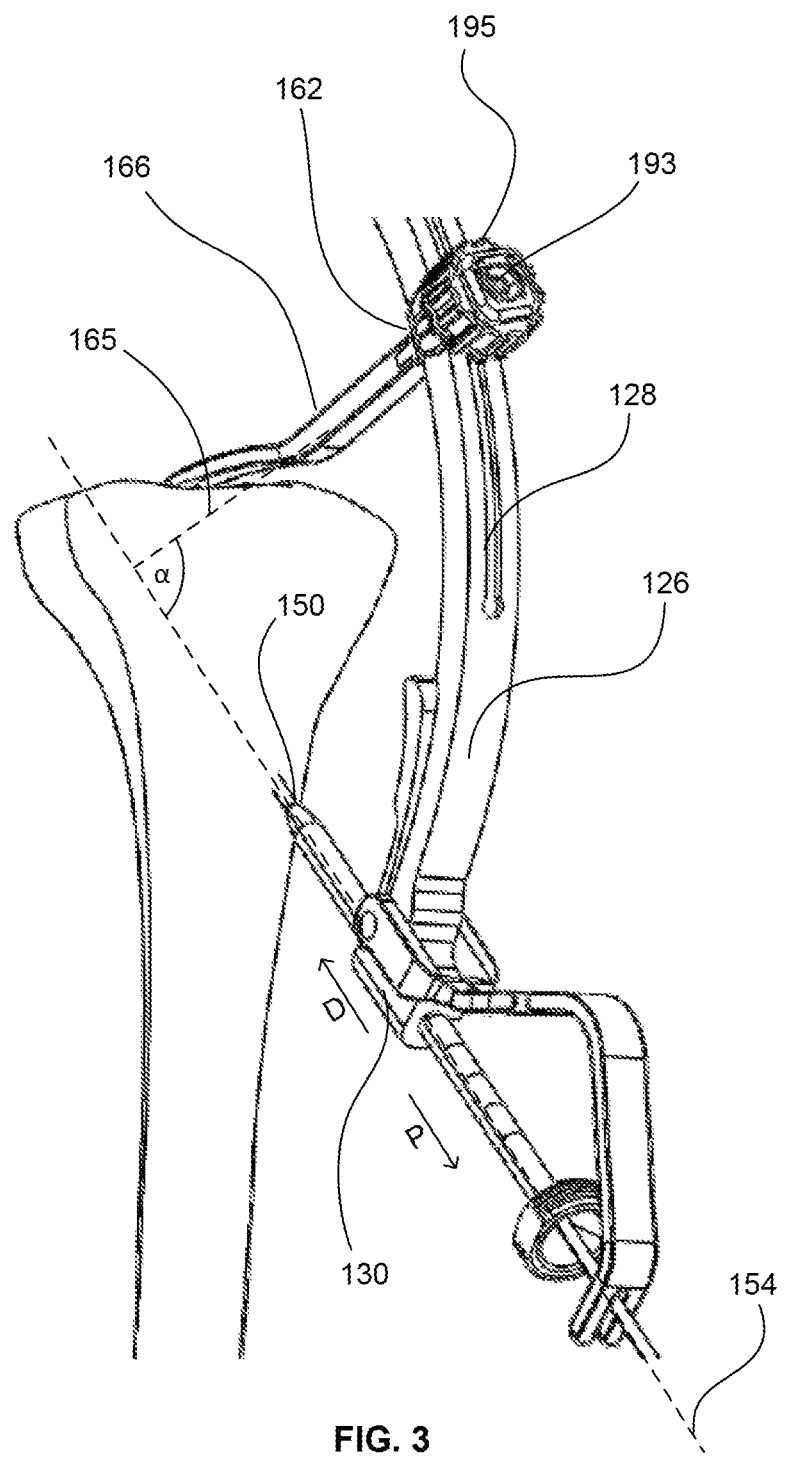
FIG. 3 is another alternate perspective view of the tibial tunnel guide of FIG. 1 showing a guide pin received in a bore hole of the elongate guide member located within a slot of the stopper member.

Referring to FIGS. 1-3, there is shown an embodiment of a tibial tunnel guide of the present invention designated generally by reference numeral 100. As shown in those figures, guide 100 is secured to a tibia 10 having an anterior side 12, a posterior side 14 and a tibial plateau 16. Guide 100 includes an arc shaped member 120, an elongate guide member 140, an alignment arm member 160 and a stopper member 180. A guide pin 190 is shown inserted into and through elongate guide member 140.

Arc shaped member 120 has a bottom surface 122 and a top surface 124. Bottom surface 122 includes an arcuate channel 126 and top surface 124 includes an arcuate recess 128 along at least a portion thereof. Arc shaped member 120 also includes a cannulated housing 130 at one end thereof and a lever arm 132 terminating at an open end 134 of cannulated housing 130. Adjacent cannulated housing 130 are first and second protrusions 136, 138 extending outwardly from arc shaped member 120.

Elongate guide member 140 has a distal portion 142, an intermediate portion 144, and a proximal portion 146. Distal portion 142 preferably tapers inwardly, intermediate portion 144 is a substantially straight portion, and proximal portion 146 preferably tapers outwardly. Distal portion 142 preferably terminates at an open serrated tip 148 having a plurality of pointed portions 150 around a circumference thereof. Elongate guide member further includes a bore hole 152 defining a longitudinal axis 154. Bore hole 152 at proximal portion 146 of elongate guide member 140 tapers inwardly such that bore hole 152 is shaped as a conical portion 154 at a proximal portion thereof.

Figure 4:
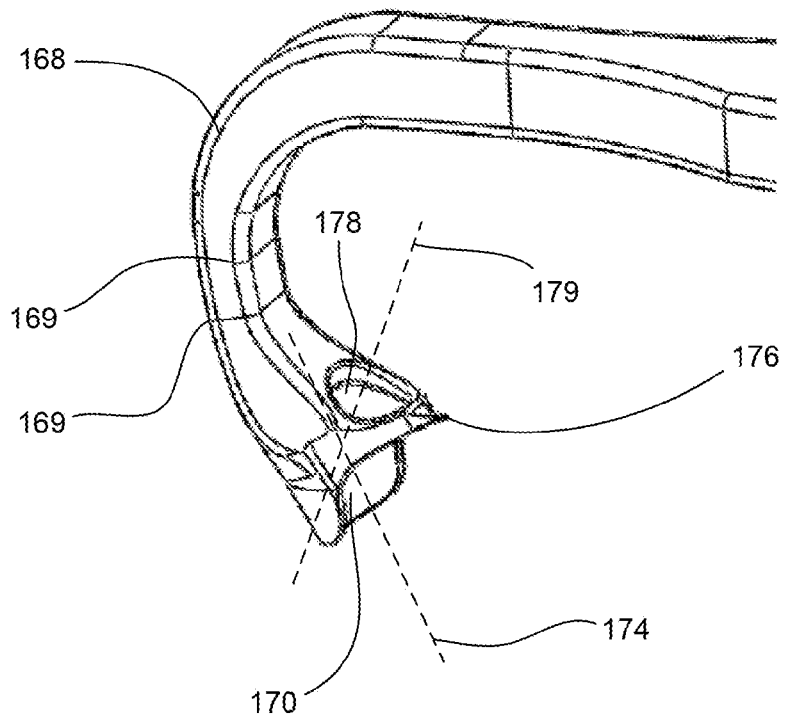
FIG. 4 is a partial view of the alignment arm member of the tibial tunnel guide shown in FIGS. 1-3.
Figure 5:
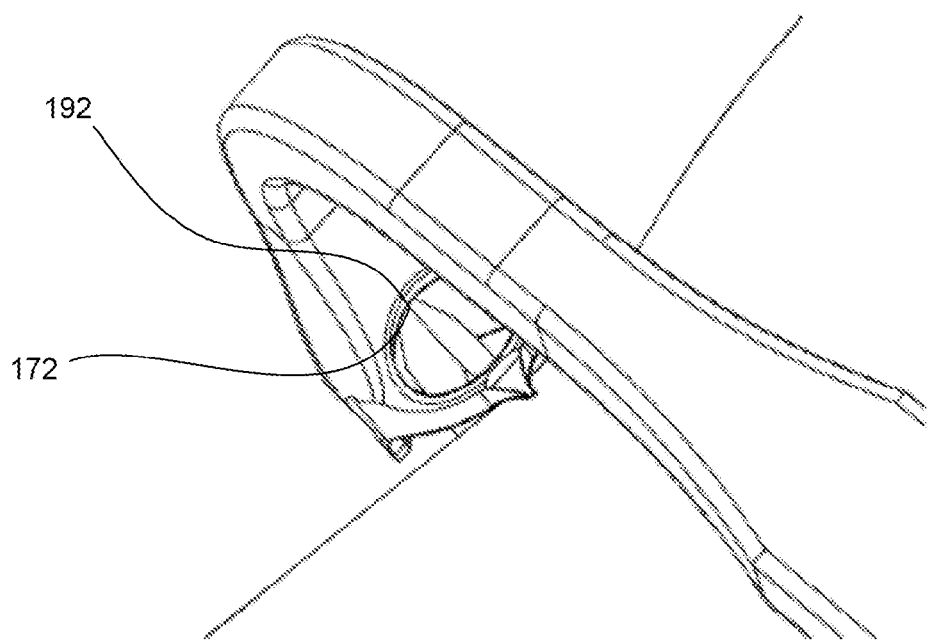
FIG. 5 is a partial view of an alignment arm member and a guide pin received with and contacting a concave blocking surface of the alignment arm member. The location of the guide pin can be viewed through a viewing aperture of the alignment arm member adjacent the concave blocking surface of the alignment arm member.

Alignment arm member 160 has a first end portion 162 and a second end portion 164. Alignment arm member 160 preferably has a substantially straight first portion 166 and a substantially curved second portion 168. The substantially curved second portion 168 is shown in detail in FIGS. 4-5. As shown in these figures, curved second portion 168 includes a plurality of marking lines 169 thereon, each of the plurality of marking lines 169 located on curved second portion 169 indicate a planar distance D from the straight first portion to a respective marking line as shown in FIG. 2. Alignment arm member 160 further includes a concave blocking surface 170 with a nadir portion 172. Central axis 174 intersects nadir portion 172 of concave blocking surface 170. Central axis 174 is preferably coaxially aligned with longitudinal axis 154 of bore hole 152 of elongate guide member 140. First end portion 162 of alignment arm member 160 terminates at a sharp tip 176 adapted to rest on bone located on posterior portion 14 of tibia 10. Alignment arm member 160 further includes a viewing aperture 178 adjacent concave blocking surface 170. Viewing aperture 178 includes an axis 179 that intersects central axis 174 of concave blocking surface 170 at an angle.

Figure 6:
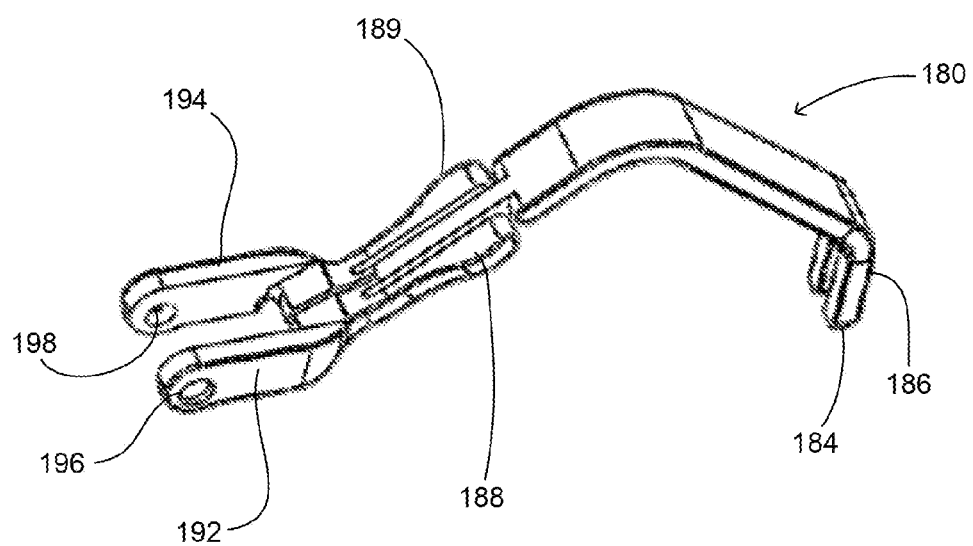
FIG. 6 is the stopper member of the tibial tunnel guide shown in FIGS. 1-3.
Figure 7:
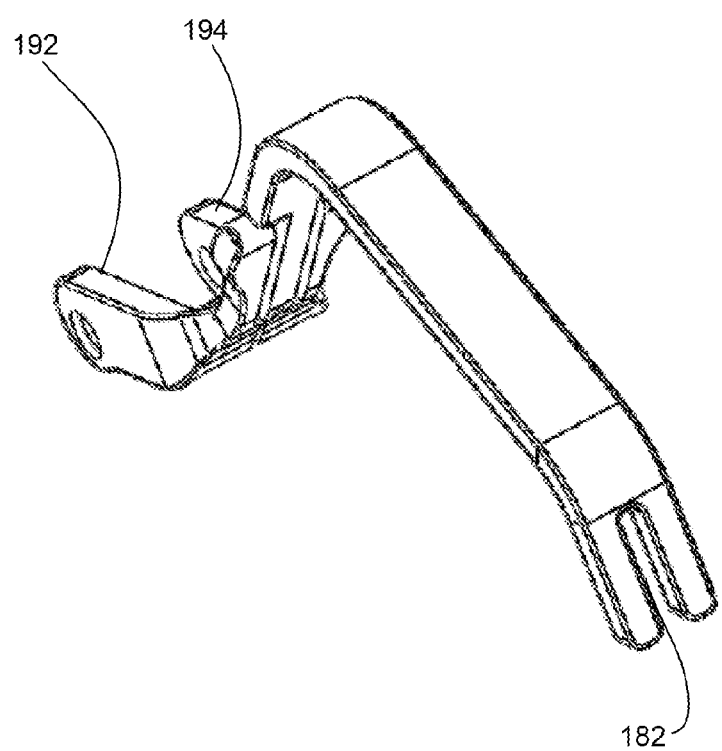
FIG. 7 is a partial view of the stopper member shown in FIG. 6.

FIG. 6 is a perspective view of stopper member 180. As shown in FIGS. 1-3, stopper member 180 is pivotably coupled to arc shaped member 120. In FIG. 1 stopper member 180 is in an undeployed position and in FIG. 2 is in a deployed position. Stopper member 180 includes an open slot 182 at a first end 184 thereof, the open slot 182 is for housing a guide pin 190 therethrough as shown in FIGS. 2-3. Stopper member further includes a proximal surface 186 substantially perpendicular to longitudinal axis 154 of bore hole 152 of elongate guide member 150. First and second lever arms 188, 189 when depressed allow first and second flanges 192, 194 having first and second apertures 196, 198 respectively to engage first and second protrusions 136, 138 of arc shaped member 120.

Figure 8:
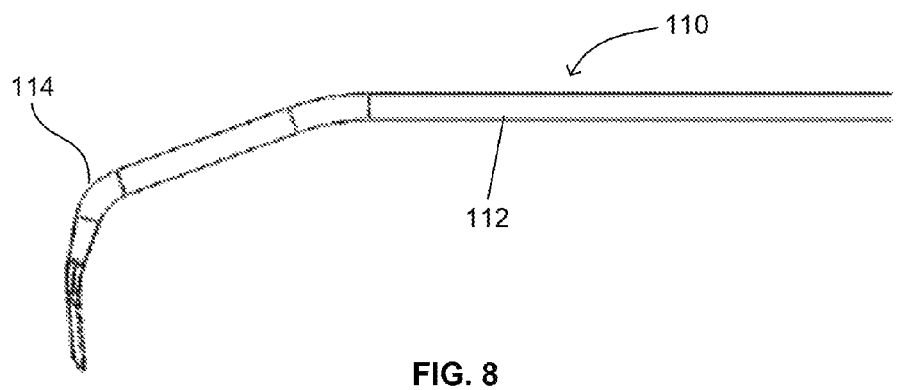
FIG. 8 is a rasp of the present invention including a rasp portion and an aperture through a neck thereof adapted to receive a distal tip of a guide pin and block the advancement of the guide pin in a distal direction.
Figures 9A, 9B:
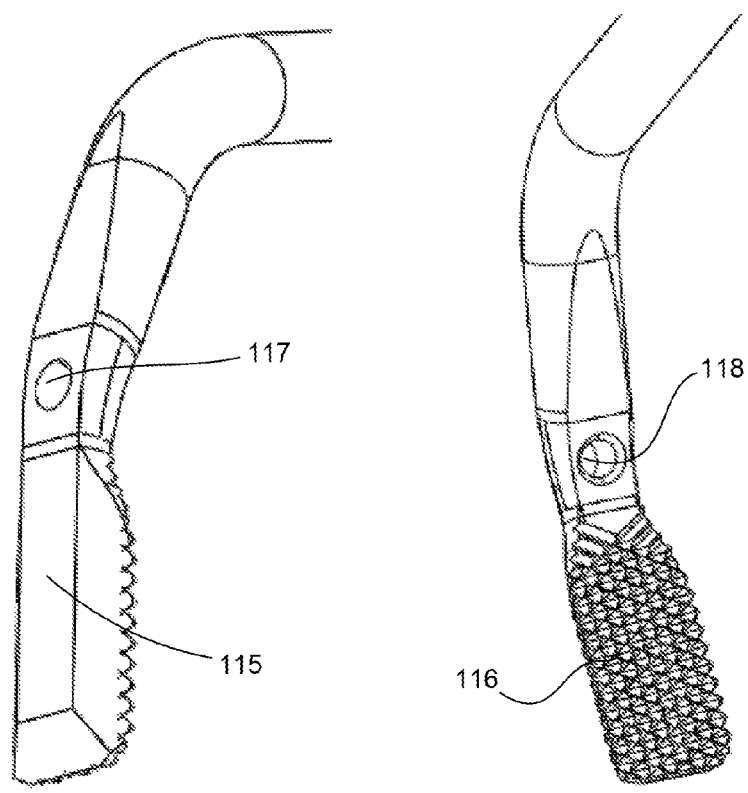
FIG. 9A is a partial view of the rasp of FIG. 8 showing the rasp features on a head portion of the rasp.
FIG. 9B is a partial view of the rasp of FIG. 8 showing the aperture on the neck portion of the rasp.

FIGS. 8-9B show a rasp 110 of the present invention. Rasp 110 includes a substantially straight portion 112 and a curved portion 114. A head portion 115 of rasp includes a rasp surface 116. Adjacent head portion 115 is an aperture 118 for receiving and housing a distal tip 192 of guide pin 190 therethrough. A diameter 117 of aperture 118 is less than a diameter 191 of guide pin 190 such that only the distal tip 192 of guide pin 190 can pass through aperture 118.

Figure 10:
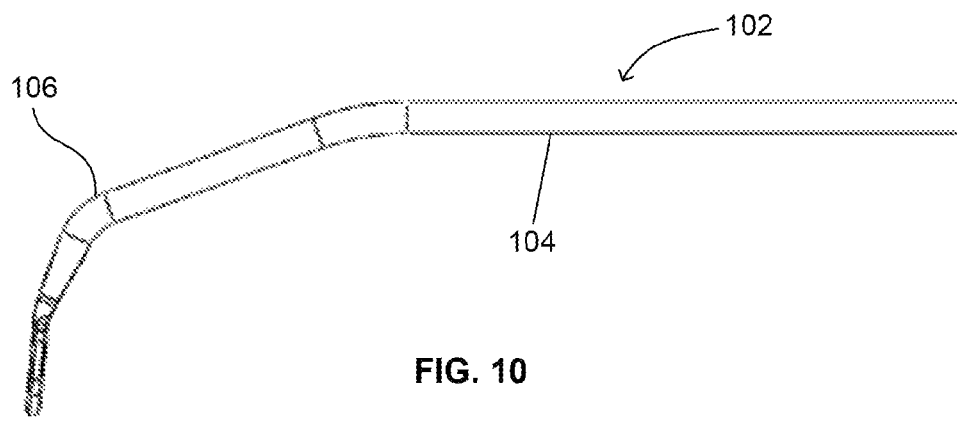
FIG. 10 is a cutter of the present invention.
Figure 11:
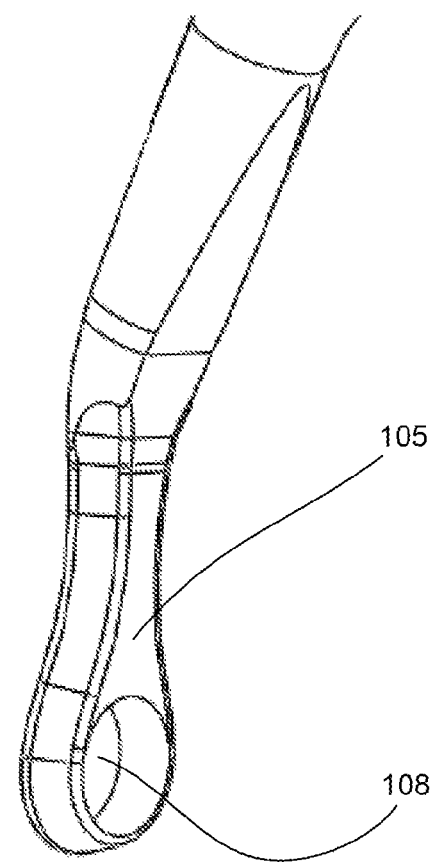
FIG. 11 is a partial view of the cutter shown in FIG. 10.

FIGS. 10-11 show a cutter or curette 102 of the present invention. Curette 102 includes a substantially straight portion 104 and a curved portion 106. A head portion 105 of curette includes an aperture 108 with a sharp edge for cutting away any PCL remnants.

One method of using drill guide 100 shown in FIGS. 1-3 includes first assembling elongate guide member 140 to arc shaped member 120 wherein a portion of intermediate portion 144 of elongate guide member 140 is held within cannulated housing 130 of arc shaped member 130. Elongate guide member 140 may move in proximal direction P and distal direction D within cannulated housing when lever arm 132 is pressed downwardly. In an upward position as shown in FIGS. 1-3, elongate guide member 140 is substantially locked in position within cannulated housing 130 of arc shaped member 120. Cannulated housing 130 is configured to guide movement of elongate guide member 140 in the proximal and distal directions, shown generally as arrows P and D respectively in FIG. 3, along longitudinal axis 154 of bore hole 152.

Next, alignment arm member 160 is coupled to arc shaped member 120. First end portion 162 of alignment arm member 160 is coupled to arc shaped member 120 and is preferably received and held within arcuate channel 122 of arc shaped member 120. A surgeon or other operating room personnel adjusts the alignment arm member 160 in channel 122 to a specific angle α corresponding to the angle between axis 165 defined by the substantially straight portion 166 of alignment arm member 160 and longitudinal axis 154 of bore hole 152 of elongate guide member 140. Angle α is generally 60°-65° but can be in a range between 30° and 120°. First end portion 162 of alignment arm member 160 is preferably secured in channel 122 of arc shaped member 120 by a screw 193 and nut 195 arrangement. Screw 193 is partially housed within arcuate recess 128 located through top surface 124 of arc shaped member 120.

Next, stopper member 180 is coupled to arc shaped member 120. First and second lever arms 188, 189 are depressed such that first and second apertures 196, 198 of first and second flanges 192, 194 are pivotably mounted on first and second protrusions 136, 138 of arc shaped member 120. Stopper member 180 is set into the deployed position shown in FIGS. 2 and 3. Guide pin 190 is then inserted though bore hole 152 of elongate guide member 140 until distal tip 192 of guide pin 190 contacts concave blocking surface 170 of alignment arm member 160. A drill (not shown) having a drill head is then inserted onto the free end of guide pin 190 until the drill head contacts the proximal surface 186 of stopper member 180. The drill head is then tightened on guide pin 190 such that the distance from the drill head to the distal tip 192 is set.

Concave blocking surface 170 may be considered a first safety mechanism such that the distal tip 192 is safely housed within concave blocking surface 170 upon exiting from the posterior portion 14 of tibia 10 rather than potentially contacting or harming delicate tissues adjacent the poster portion 14 of tibia 10 upon exiting therefrom. The stopper member 180 thusly acts as a second safety mechanism such once the drill head contacts the proximal surface 186 of stopper member 180, the guide pin or drill cannot move any further in the distal direction and therefore can only exit from the posterior portion 14 of the tibia 10 a known amount that protects tissues adjacent the poster portion 14 of tibia 10 from being contacted or damaged.

Once the drill head is tightened on guide pin 190, guide pin 190 is advanced back through bore hole 152 in a proximal direction and removed from elongate guide member 140. At this time, the surgeon may size the graft replacement. The graft (not shown) is generally a 9-10 mm diameter soft tissue allograft, but can be less than 9 mm in diameter or more than 10 mm in diameter. The surgeon generally uses the curette or shaver 102 shown in FIGS. 10-11 and a radio frequency ("RF") device (not shown) to remove any remnants of the damaged or torn PCL left in the knee joint. Any remaining PCL footprint may be liberated using rasp surface 116 of rasp 110. A footprint surface 17 of tibia 10 should be rasped until bleeding occurs in the region. Bleeding generally helps to promote healing and tissue growth in the region potentially during surgery and also after the surgical procedure has been completed.

Alignment arm member 160 is then inserted into the joint space of the knee. An underside of alignment arm member 160 is preferably lied flat again tibial plateau 16 of tibia 10. This gives an approximate distance D of the exit point of distal tip 192 of guide pin 190 from the posterior portion 14 of tibia 10 to the tibial plateau 16. Sharp tip 176 of alignment arm member 160 can be used to engage the posterior portion 14 of tibia 10 adjacent the native PCL insertion location or concave blocking surface 170 can be used to lie directly on the native PCL footprint.

After alignment arm member 160 is stabilized on posterior portion 14 of tibia 10, lever arm 132 is depressed and elongate guide member 140 is moved distally until open serrated tip 148 contacts anterior portion 12 of tibia 10. Guide pin 190 tightly mounted to drill head of drill is then inserted back through bore hole 152 of elongate guide member 140 and is drilled through the tibia until distal tip 192 contacts concave blocking surface 170 of alignment arm member 160. If the guide pin is correctly advanced through the tibia, distal tip 192 should be visible through viewing aperture 178. An axis 179 of aperture 178 is preferably not aligned with axis 174 such that distal tip 192 cannot exit aperture 178 when guide pin 190 is moving in a distal direction. Aperture 178 is specifically designed for viewing the location of distal tip 192 of guide pin 190 and not as a location for distal tip 192 to exit concave blocking surface 170 of alignment arm member 160.

Preferably, distal tip 192 contacts a nadir portion 172 of concave blocking surface 170 adapted to block distal tip 192 of guide pin 190 a predetermined distance from proximal surface 186 of stop member 180 along longitudinal axis 154 of bore hole 152 of elongate guide member 140. Preferably, a longitudinal axis 174 defined by distal tip 192 contacting nadir portion 172 of concave blocking surface 170 is coaxially aligned with longitudinal axis 154. In some procedures, an exit location of distal tip 192 of guide pin 190 has an axis that is not aligned with longitudinal axis 154 of bore hole 152 of elongate guide member 140, and therefore, distal tip 192 of guide pin 190 may contact concave blocking surface 170 of alignment arm member 160 at a location having an axis that is not aligned with longitudinal axis 154.

After guide pin 190 exits posterior portion 14 of tibia 10, stopper member 180 and elongate guide member 140 may now be removed from arc shaped member 120, leaving arc shaped member 120, alignment arm member 160, and guide pin 190 in place. Arc shaped member 120 and alignment arm member 160 can then be removed leaving guide pin 190 in place. Distal tip 192 should then be covered by aperture 118 of rasp 110 to impeded movement of guide pin 190 in the distal direction. Guide pin 190 can now be used to guide the drilling of the tibial tunnel using a drill with a 9 mm diameter. While it is preferable to use a drill with a 9 mm diameter, drills having smaller or larger diameters than 9 mm may be used. Upon drill exiting the posterior portion 14 of tibia 10, edges of the tunnel exit can be chamfered using cutter 102 or other cutting instrument.

Referring to FIGS. 12-15, there is shown an embodiment of a femoral tunnel guide of the present invention designated generally by reference numeral 200. As shown in those figures, guide 200 is secured to a femur 110 having an anterior side 112, a posterior side 114 and first and second condyles 116, 118 are either a medial or lateral condyle depending on whether the PCL replacement surgery is occurring on the left or the right knee. First and second condyles 226, 118 each include a cartilage line 115.

Figure 12:
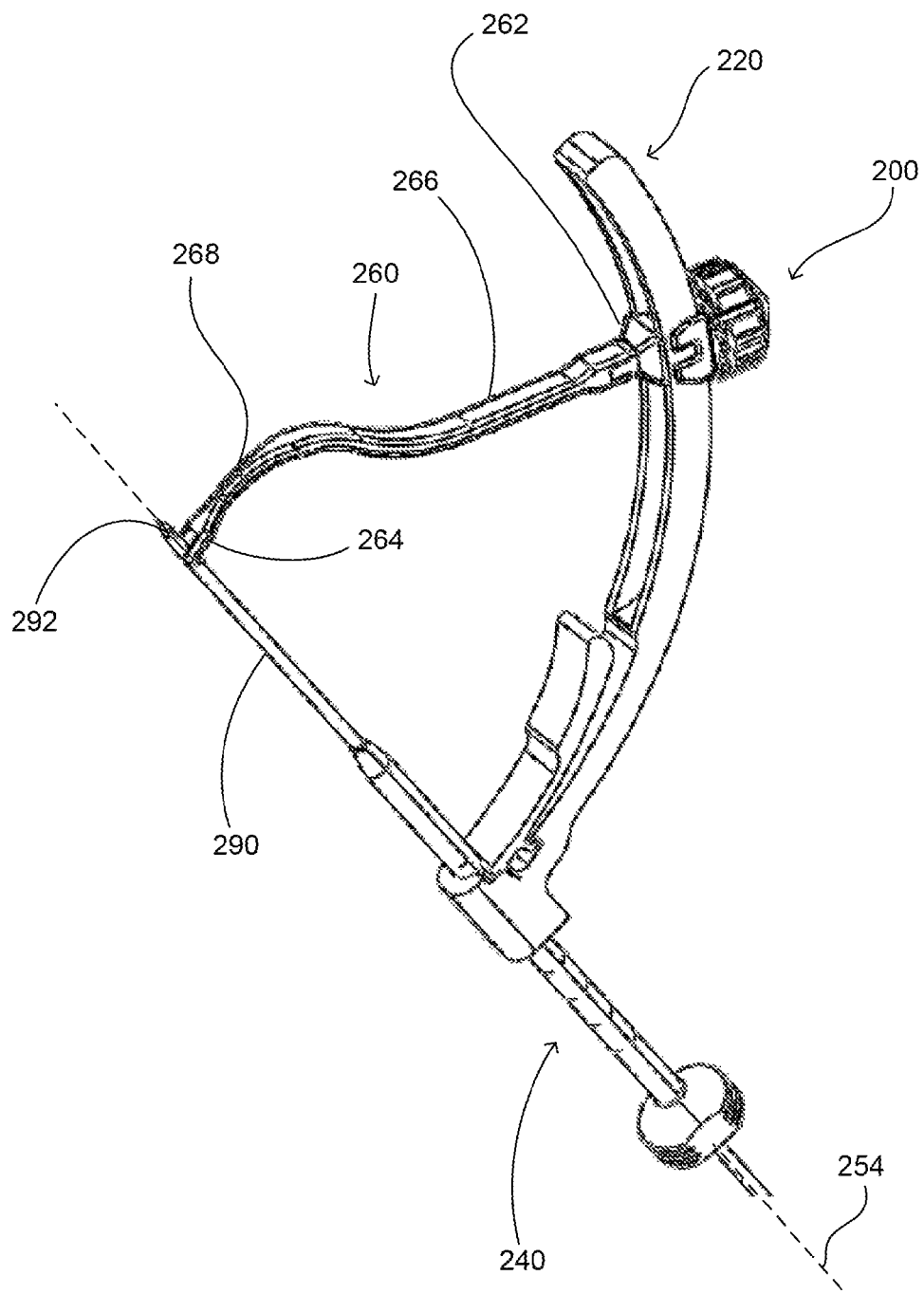
FIG. 12 is a perspective view of a femoral tunnel guide having an arc shaped member, an elongate guide member, a femoral alignment arm member and a stopper member.
Figure 13:
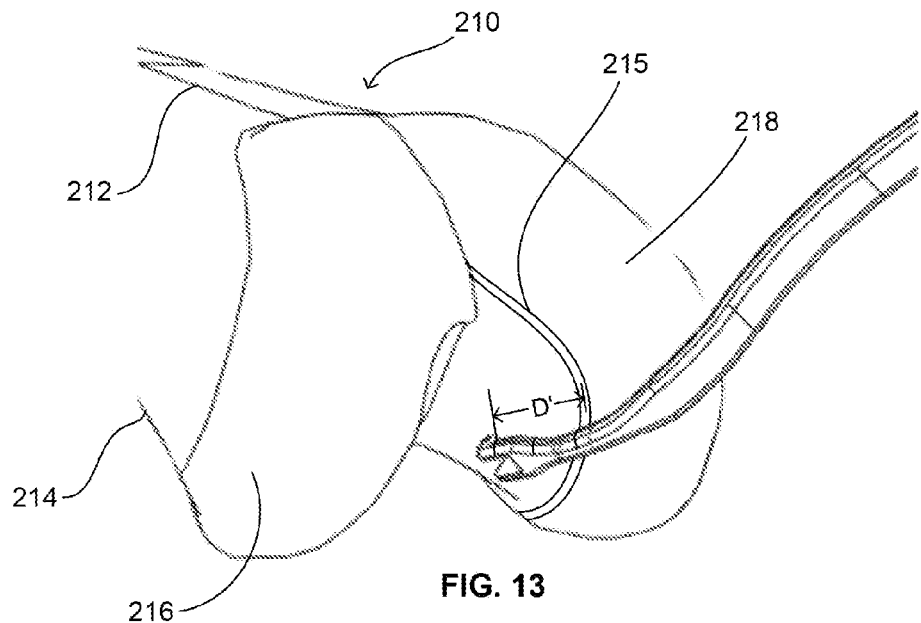
FIG. 13 is a partial view of the femoral alignment arm of the femoral tunnel guide shown in FIG. 12 positioned between the medial and lateral condyles of a femur.
Figure 14:
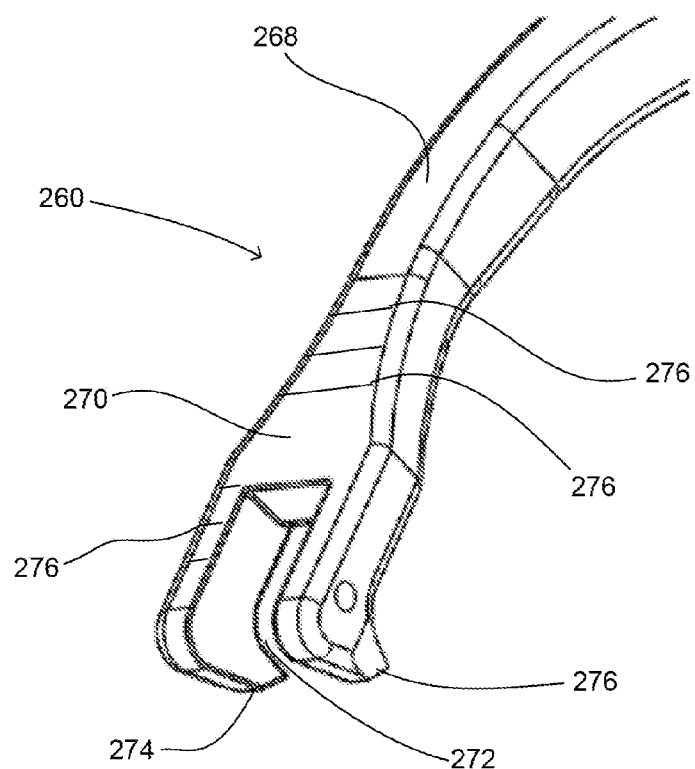
FIG. 14 is an alternate partial view of the femoral alignment arm of the femoral tunnel guide shown in FIG. 12.

As shown in FIG. 12, guide 200 includes an arc shaped member 220, an elongate guide member 240, an alignment arm member 260 and a stopper member 280 (not shown). A guide pin 290 is shown inserted into and through elongate guide member 240. FIG. 13 shows a portion of femur 210 and femoral alignment arm 260 positioned between condyles 216, 218 of femur 210. Condyles 216, 218 each include a cartilage line 215 that can be used to measure the distance of the exit location of guide pin 290 from the femur.

Alignment arm member 260 has a first end portion 262 and a second end portion 264. Alignment arm member 260 preferably has a substantially straight first portion 266 and a substantially curved second portion 268. The substantially curved second portion 268 is shown in detail in FIGS. 13-15. As shown in these figures, curved second portion 268 includes a plurality of marking lines 276 thereon, each of the plurality of marking lines 276 located on curved second portion 268 indicate a planar distance D' from cartilage line 215 to a respective marking line 276 as shown in FIG. 13. Alignment arm member 260 further includes first and second distal tips 274, 276 for engaging bone of femur 210 adjacent condyles 216, 218. Alignment arm member 260 also includes a recess 272 for receiving distal tip 292 of guide pin 290 therethrough.

In a method of using drill guide 200 shown in FIGS. 12-15, elongate guide member 240, alignment arm member 260 and stopper member 280 (not shown) are attached to arc shaped member 220 in a similar manner as elongate guide member 140, alignment arm member 160 and stopper member 180 are attached to arc shaped member 120.

When alignment arm member 260 is positioned in arc shaped member 220, a surgeon or other operating room personnel adjusts alignment arm member 260 with respect to arc shaped member 220 such that $\alpha$ is generally 65°-75° but can be in a range between 30° and 120°.

Figure 15:
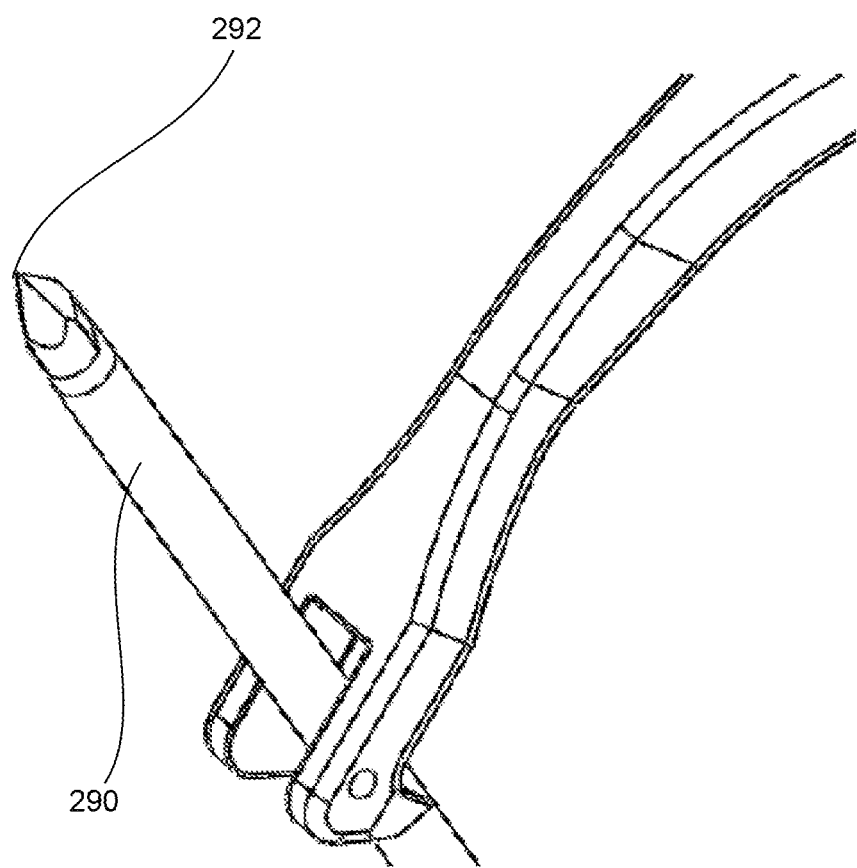
FIG. 15 is another alternative partial view of the femoral alignment arm of the femoral tunnel guide shown in FIG. 12 having a guide pin located in a recess in a head portion of the femoral alignment arm.

As described above, once a drill head of a drill is tightened on guide pin 290, guide pin 290 is advanced back through bore hole 252 in a proximal direction and removed from elongate guide member 240. Alignment arm member 260 is then inserted through an anterior medial portal adjacent the intercondylar notch of condyles 216, 218. Markings 276 on alignment arm member 260 indicate the distance D' from guide pin 290 exit into the intercondylar notch. Preferably, guide pin 290 exits from intercondylar notch and through recess 272 of head portion 270 of alignment arm member 260 as shown in FIG. 15. D' approximates the distance a drill will exit the intercondylar notch from cartilage line 215. Guide pin 290 can now be used to guide the drilling of the femoral tunnel using a drill with a 10 mm diameter. While it is preferable to use a drill with a 10 mm diameter, drills having smaller or larger diameters than 10 mm may be used.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A drill guide assembly for arthroscopic surgery, comprising:
    a guide pin;
    an arc shaped member;
    an elongate guide member coupled to the arc shaped member, the elongate guide member having a bore hole therethrough for receiving the guide pin, the bore hole defining a longitudinal axis; and
    an alignment arm having a substantially straight first end portion and a substantially curved second end portion, the first end portion coupled to the arc shaped member and the second end portion including a first part and a second part, the first part of the second end portion defining a concave blocking surface, wherein the longitudinal axis of the bore hole passes through the concave blocking surface so that the guide pin, when inserted into the bore hole, contacts the concave blocking surface and is prevented from moving past the concave blocking surface, wherein the second part of the second end portion defines a viewing aperture through which at least a portion of the concave blocking surface is viewable, and wherein upon contacting the guide pin in the concave blocking surface, a distal portion of the guide pin is viewable through the viewing aperture.

2. The drill guide assembly of claim 1, wherein the arc shaped member includes a cannulated housing adapted to receive a portion of the elongate guide member therein and guide movement of the elongate guide member in a proximal direction and the distal direction along the longitudinal axis of the bore hole.

3. The drill guide assembly of claim 1, wherein the elongate guide member has a distal portion and a proximal portion, the distal portion being tapered inwardly and the proximal portion being tapered outwardly.

4. The drill guide assembly of claim 3, wherein the distal portion of the elongate guide member terminates at an open serrated tip having a plurality of pointed portions around a circumference thereof.

5. The drill guide assembly of claim 1, wherein the second end portion of the alignment arm has a sharp tip.

6. The drill guide assembly of claim 1, wherein the viewing aperture has a central axis that intersects the longitudinal axis of the bore hole of the elongate guide member at a point adjacent to the concave blocking surface.

7. The drill guide assembly of claim 1, further comprising a stopper member pivotably coupled to the arc shaped member.

8. The drill guide assembly of claim 7, wherein the stopper member includes an open slot at a first end thereof, the open slot adapted to house the guide pin therethrough.

9. The drill guide assembly of claim 8, wherein the stopper member has a proximal surface substantially perpendicular to the longitudinal axis of the bore hole of the elongate guide member to limit the insertion depth of the guide pin.

10. The drill guide assembly of claim 1, wherein the second portion includes a plurality of marking lines thereon, each of the plurality of marking lines located on the second portion indicating a predefined distance, in a direction transverse to a longitudinal axis of the alignment arm, between a point on the alignment arm and the marking line.

11. The drill guide assembly of claim 1, wherein the arc shaped member includes an arcuate channel adapted to slidably secure the alignment arm in the channel when the alignment arm is coupled to the arc shaped member.

12. The drill guide assembly of claim 1, wherein a projection extends away from the concave blocking surface, such that at least a portion of a perimeter of the projection partially defines the extent of the viewing aperture.

13. The drill guide assembly of claim 12, wherein the perimeter of the projection is substantially closed, such that a surface of the projection is engageable with the guide pin once the guide pin is seated in the concave blocking surface to prevent movement of the guide pin away from the blocking surface and past the surface.

14. A drill guide assembly for arthroscopic surgery, comprising:
    a guide pin;
    an arc shaped arm;
    an elongate guide coupled to the arc shaped arm, the elongate guide having an internal bore adapted to receive the guide pin, the internal bore having a longitudinal central axis; and
    an alignment arm having a first substantially straight portion extending away from the arc shaped arm along a longitudinal axis and a second substantially curved portion offset from the first portion, the second portion of the alignment arm defining a concave blocking surface, wherein the longitudinal central axis of the bore hole passes through the concave blocking surface so that the guide pin, when inserted into the bore hole, contacts the concave blocking surface and is prevented from moving past the concave blocking surface, the second portion of the alignment arm further defining a viewing aperture through which at least a portion of the concave blocking surface is viewable, wherein the second portion has at least one marking line that indicates a predefined distance, in a direction transverse to the longitudinal axis of the first portion of the alignment arm, between a point on the first portion of the alignment arm and the marking line.

15. The drill guide assembly of claim 14, wherein the second portion of the alignment arm includes a plurality of marking lines, each of the marking lines indicating a predefined distance, in a direction transverse to the longitudinal axis of the first portion of the alignment arm, between a point on the first portion of the alignment arm and the respective marking line.

16. The drill guide assembly of claim 14, wherein a projection extends away from the concave blocking surface, such that at least a portion of a perimeter of the projection partially defines the extent of the viewing aperture.

17. The drill guide assembly of claim 16, wherein a portion of the projection forms a sharpened tip.

18. The drill guide assembly of claim 14, wherein the at least one marking line is usable to determine the exit location of the pin relative to a tibial plateau of a patient.

19. The drill guide assembly of claim 14, further comprising a stopper member pivotably coupled to the arc shaped arm, the stopper member defining a stop surface arranged transverse to the longitudinal axis of the internal bore of the elongate guide, wherein the stop surface is adapted to limit the insertion depth of the guide pin.

\* \* \* \* \*